(12) United States Patent
Soroida et al.

(10) Patent No.: US 11,517,287 B2
(45) Date of Patent: Dec. 6, 2022

(54) TISSUE ELASTICITY MEASUREMENT DEVICE AND MEASUREMENT METHOD

(71) Applicant: THE UNIVERSITY OF TOKYO, Bunkyo-ku (JP)

(72) Inventors: Yoko Soroida, Bunkyo-ku (JP);
Takuma Nakatsuka, Bunkyo-cho (JP);
Masaya Sato, Bunkyo-cho (JP);
Hayato Nakagawa, Bunkyo-cho (JP);
Hitoshi Ikeda, Bunkyo-cho (JP);
Kazuhiko Koike, Bunkyo-cho (JP);
Yutaka Yatomi, Bunkyo-cho (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 322 days.

(21) Appl. No.: 16/490,397

(22) PCT Filed: Mar. 7, 2018

(86) PCT No.: PCT/JP2018/008758
§ 371 (c)(1),
(2) Date: Nov. 12, 2019

(87) PCT Pub. No.: WO2018/164181
PCT Pub. Date: Sep. 13, 2018

(65) Prior Publication Data
US 2020/0245974 A1 Aug. 6, 2020

(30) Foreign Application Priority Data
Mar. 7, 2017 (JP) .............................. JP2017-042460

(51) Int. Cl.
*A61B 8/08* (2006.01)
*A61B 8/06* (2006.01)

(52) U.S. Cl.
CPC ............... *A61B 8/485* (2013.01); *A61B 8/06* (2013.01); *A61B 8/085* (2013.01); *A61B 8/488* (2013.01); *A61B 8/5223* (2013.01)

(58) Field of Classification Search
CPC ........... A61B 8/485; A61B 8/06; A61B 8/085; A61B 8/488; A61B 8/5223; A61B 8/5207; A61B 8/08
See application file for complete search history.

(56) References Cited

U.S. PATENT DOCUMENTS

| | | | | |
|---|---|---|---|---|
| 4,182,173 A | * | 1/1980 | Papadofrangakis | ..... A61B 8/00 600/441 |
| 6,409,671 B1 | * | 6/2002 | Eriksen | ..................... A61B 8/13 600/458 |

(Continued)

FOREIGN PATENT DOCUMENTS

| JP | 2006-325746 | 12/2006 |
|---|---|---|
| JP | 2012-105838 | 6/2012 |

(Continued)

OTHER PUBLICATIONS

Search Report dated Nov. 26, 2020 issued in European Patent Application No. 18763561.0.

(Continued)

*Primary Examiner* — Bo Joseph Peng
(74) *Attorney, Agent, or Firm* — Cozen O'Connor

(57) ABSTRACT

There is provided a tissue elasticity measurement device 100 and a measurement method that allow for quantitative evaluation of biological changes related to tissue elasticity such as liver fibrosis. The tissue elasticity measurement device 100 has a supersonic wave measuring instrument 100a that measures a pulse waveform corresponding to a blood flow velocity by a pulse wave Doppler method, and an information processor 100b that calculates a deviation index value corresponding to a coefficient of variation from a pulse waveform obtained by the supersonic wave measuring instrument 100a.

6 Claims, 13 Drawing Sheets

(56) References Cited

U.S. PATENT DOCUMENTS

2003/0069508 A1* 4/2003 Kawaguchi .............. A61B 8/06
600/500
2003/0109785 A1 6/2003 Buck et al.
2016/0199029 A1* 7/2016 Struijk .................... A61B 8/06
600/438

FOREIGN PATENT DOCUMENTS

JP 2012-170748 9/2012
JP 2014-210121 11/2014

OTHER PUBLICATIONS

Salvatore et al., "Relationship between hepatic haemodynamics assessed by Doppler ultrasound and liver stiffness," Digestive and Liver Disease, W.B. Saunders, GB, Aug. 22, 2011, pp. 154-159, vol. 44, No. 2.
Office Action dated Jul. 1, 2020 issued in Japanese Patent Application No. 2019-504635.
N. Shinozuka et al., "Evaluation of Hepatic Venous Flow in Liver Cirrhosis Using Doppler Echography", Journal of Japanese College of Surgeons, vol. 23, No. 5, Oct. 1998, pp. 784-788.
T. Sekimoto et al., "Liver Stiffness: A Significant Relationship with the Waveform Pattern in the Hepatic Vein", Ultrasound in Med. & Biol., vol. 41, No. 7, pp. 1801-1807, 2015, http://dx.doi.org/10.1016/j.ultrasmedbio.2015.03.002.

* cited by examiner

NOTE: LOGARITHMIC AXIS

TISSUE ELASTICITY MEASUREMENT DEVICE AND MEASUREMENT METHOD

TECHNOLOGICAL FIELD

The present invention relates to a measurement device and a measurement method that allow for quantification of tissue elasticity, and particularly to a tissue elasticity measurement device and a measurement method that facilitate quantitative evaluation of biological changes such as liver fibrosis.

BACKGROUND

For example, it is known that chronic hepatitis may develop to hepatic cirrhosis, and eventually to hepatocellular carcinoma and, in medical treatment of liver, liver fibrosis evaluation is very important for grasping the pathological condition of hepatitis, selection of treatment, evaluation of liver cancer risk, or the like. Although pathological tissue images taken by liver tissue biopsy is regarded as an evaluation standard in evaluation methods of liver fibrosis, there is a problem that it can evaluate only one point of the liver due to its high invasiveness. In addition, there exists a non-invasive fibrosis estimation method called elastography, such as transient elastography (for example, Fibro Scan (registered trademark)), or the like that measures the liver stiffness. However, elastography is not widely used due to its expensive device. Furthermore, there is a problem with liver stiffness measurement by elastography in that existence of inflammation or congestion in the liver may affect the measurement value, making it impossible to measure the correct value. Moreover, obesity or narrow intercostal space obesity may prevent measurement.

There is a method for measuring blood flow velocity called "pulse wave Doppler method", and it is known that hepatic vein waveforms obtained using the pulse wave Doppler method relate to liver fibrosis (Non Patent Literature 1). However, determination of liver fibrosis by the pulse wave Doppler method remains to be qualitative determination of hepatic vein waveform conditions by eyesight, with no quantitative evaluation being performed.

Various schemes for detecting supersonic echoes have been proposed as common ultrasonic wave diagnosis methods, and there is known one that not only simply obtains echo images, for example, but also calculates a coefficient of variation CV that reflects the degree of dispersion of amplitude from echo data or supersonic wave image data in order to analyze the tissue property (for example, Patent Literature 1 and 2). However, such a scheme merely performs image processing of supersonic echoes, with no evaluation of the tissue elasticity of internal organs such as evaluation of liver fibrosis.

CITATION LIST

Non Patent Literature

Non-Patent Literature 1: Liver Stiffness: A Significant Relationship with the Waveform Pattern in the Hepatic Vein. Sekimoto T et al., Ultrasound in Medicine & biology 2015

Patent Literature

Patent Literature 1: Japanese Patent Laid-Open No. 2012-105838
Patent Literature 2: Japanese Patent Laid-Open No. 2014-210121

SUMMARY

The present invention, which has been made in view of the aforementioned background technology, is intended to provide a tissue elasticity measurement device and a measurement method that allow for quantitative evaluation of biological changes related to tissue elasticity such as liver fibrosis.

In order to achieve the aforementioned object, the tissue elasticity measurement device according to the present invention has a supersonic wave measuring instrument that measures a pulse waveform corresponding to a blood flow velocity by the pulse wave Doppler method, and an information processor that calculates a deviation index value corresponding to a coefficient of variation from a pulse waveform obtained by the supersonic wave measuring instrument.

In the aforementioned tissue elasticity measurement device, the information processor calculates a deviation index value corresponding to the coefficient of variation from a pulse waveform obtained by the pulse wave Doppler method, and therefore allows for quantitatively evaluating changes in the shape of the pulse waveform with a good reproducibility. The coefficient of variation of the pulse waveform corresponding to the shape of the pulse waveform tends to become smaller with increasing tissue elasticity such as liver fibrosis, for example, and the use of the coefficient of variation of the pulse waveform or deviation index value makes it easier to evaluate an increase in the tissue elasticity, and further the degree of progress of a disease or change of the biological tissue. It has been confirmed that the deviation index value corresponding to the coefficient of variation is hardly affected by inflammation or congestion in the site of interest, and unaffected by individual differences in blood flow velocity.

In another aspect of the present invention, the information processor of the aforementioned tissue elasticity measurement device has a waveform processor that determines at least one of: the absolute maximum flow velocity, the maximum value, the minimum value, and the mean value at each time phase of the pulse waveform, and calculates the coefficient of variation from at least one of the absolute maximum flow velocity, the maximum value, the minimum value, and the mean value. In such a case, characteristics of the pulse waveform can be extracted except for the fluctuating component or the noise component of the velocity in the pulse waveform.

In yet another aspect of the present invention, the waveform processor extracts an envelope so as to conform to a standard three-phase pulse waveform having a retrograde first waveform part with an ascending peak of the flow velocity, an antegrade second waveform part with a descending peak of the flow velocity, and an antegrade third waveform part with a descending peak of the flow velocity during a heartbeat period, and calculates the coefficient of variation therefrom. For example, with a normal hepatic vein waveform typically having the first to the third waveform parts described above, there is a tendency that the first waveform part is lost as liver fibrosis progresses, then the boundary between the second and the third waveform parts is lost as the liver fibrosis further progresses, so that an envelope or a trace waveform conforming to the first to the third waveform parts ensures evaluation of the degree of progress of liver fibrosis.

In yet another aspect of the present invention, an envelope is extracted at a high-velocity side of the absolute value of the first waveform part when there exists the first waveform part, an envelope is extracted at the high-velocity side of the absolute value of the second waveform part when there exists the second waveform part, and an envelope is extracted at the high-velocity side of the absolute value of the third waveform part when there exists the third waveform part. In such a case, it becomes possible to perform measurement with characteristics of waveforms of the first to the third waveform parts having been accurately extracted.

In yet another aspect of the present invention, the CV value standing for coefficient of variation, is given by the following expression:

$$CV = \frac{\sqrt{\left|\frac{1}{n}\sum_{i=1}^{n}(V_i - V_{m\_peak})^2\right|}}{V_{m\_peak}}$$

where, n is the number of samples of the pulse waveform, $V_i$ is the blood flow velocity, and $V_{m\_peak}$ is the mean value of the blood flow velocity.

In yet another aspect of the present invention, the information processor measures a deviation index value from a pulse waveform corresponding to a plurality of heartbeat periods. In such a case, it is possible to further increase the reliability of the deviation index value obtained.

In yet another aspect of the present invention, the supersonic wave measuring instrument uses fast Fourier transform to generate, from the Doppler component, a measurement value of the flow velocity for each time resolution.

In yet another aspect of the present invention, the supersonic wave measuring instrument measures the vein waveform of the liver. In such a case, it is possible to evaluate the degree of progress of liver fibrosis.

In order to achieve the aforementioned object, the tissue elasticity measurement method according to the present invention is a measurement method for obtaining a pulse waveform corresponding to a blood flow velocity by the pulse wave Doppler method, and calculating a deviation index value corresponding to a coefficient of variation from a pulse waveform obtained by measurement.

The aforementioned tissue elasticity measurement method calculates the deviation index value corresponding to the coefficient of variation from the pulse waveform obtained by the pulse wave Doppler method and therefore allows for quantitatively evaluating changes in the shape of the pulse waveform with a good reproducibility. The coefficient of variation of the pulse waveform corresponding to the shape of the pulse waveform tends to become smaller with increasing tissue elasticity such as liver fibrosis, for example, and the use of the coefficient of variation of the pulse waveform or deviation index value makes it easier to evaluate an increase in the tissue elasticity, and further the degree of progress of a disease or change of the biological tissue.

DETAILED DESCRIPTION OF EMBODIMENTS

A tissue elasticity measurement device and a measurement method of an embodiment according to the present invention will be described below, referring to FIG. 1, or the like.

Figure 1:
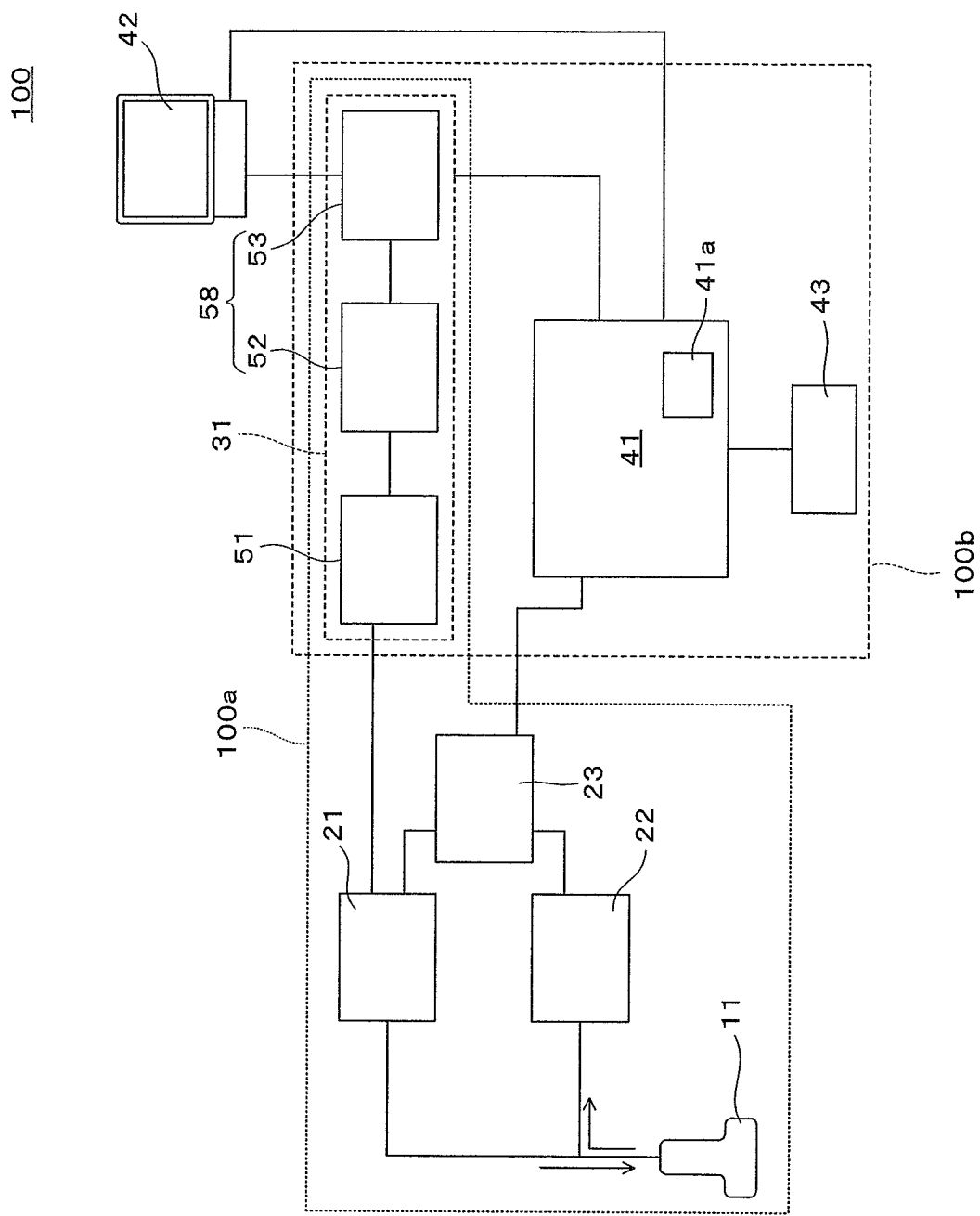
FIG. 1 is a block diagram explaining a tissue elasticity measurement device of an embodiment.

A tissue elasticity measurement device 100 illustrated in FIG. 1 has a supersonic wave probe 11, a transmitter 21, a receiver 22, a drive controller 23, a signal processor 31, a main controller 41, a display 42, and an operation panel 43. Of the foregoing components, the supersonic wave probe 11, the transmitter 21, the receiver 22, the drive controller 23, and the signal processor 31 form a supersonic wave measuring instrument 100a that measures the pulse waveform corresponding to the blood flow velocity by the pulse wave Doppler method. In addition, the signal processor 31, the main controller 41 and the operation panel 43 form an information processor 100b that calculates the deviation index value corresponding to the coefficient of variation (specifically, CV value) from the pulse waveform obtained by the supersonic wave measuring instrument 100a.

The transmitter 21 drives the supersonic wave probe 11 to transmit supersonic wave pulses into a subject at a periodic timing, and the receiver 22 drives the supersonic wave probe 11 to receive supersonic echoes from the subject. The drive controller 23 controls the periodic transmission operation of supersonic wave pulses by the transmitter 21, and also controls the reception operation of supersonic echoes by the receiver 22 synchronized therewith.

The signal processor 31 includes a Doppler processor 51, a fast Fourier transformer 52, and a waveform calculator 53. Here, the Doppler processor 51 performs filtering such as phase detection, sample holding and low-frequency cutting, and extracts, from the supersonic echoes, a Doppler component, i.e., frequency shift, caused by the blood flow in a sample region among targets in the subject. The fast Fourier transformer 52 calculates frequency spectrum data by performing a frequency analysis according to fast Fourier transform on the Doppler component, i.e., frequency shift, obtained by the Doppler processor 51. The waveform calculator 53 forms a Doppler waveform from the frequency spectrum data obtained by the fast Fourier transformer 52 and outputs the waveform to a display 42 in a displayable state. Here, the Doppler waveform is a pulse waveform representing the blood flow velocity of a vein or an artery. The pulse waveform is represented with time along the horizontal axis and blood flow velocity along the vertical axis. The fast Fourier transformer 52 and the waveform calculator 53 included in a pulse waveform generator 58 generate, from the Doppler component, a measurement value of the flow velocity for each time resolution using fast Fourier transform. The Doppler component or the blood flow velocity may be subjected to correction processing in the pulse waveform generator 58, taking into account the incident angle of the supersonic wave due to arrangement of the supersonic wave probe 11 and the like. The pulse waveform generator 58 functions as a vein waveform generator specifically when a vein is the target of measurement, for example.

The signal processor 31 has also a function of converting, with or without rendering, a supersonic echo (i.e., amplitude thereof, or the like) which has not been processed by the pulse wave Doppler method, into two-dimensional image data. The signal processor 31 outputs a tomographic echo image corresponding to the supersonic echo to the display 42 in a displayable state.

The main controller 41 functions as a waveform processor that determines at least one of: the absolute maximum flow velocity, the maximum value, the minimum value, and the mean value at each time phase of the pulse waveform. The main controller 41 collectively controls the operation of the drive controller 23, the signal processor 31, the display 42, or the like. The main controller 41 obtains a supersonic echo from the target by appropriately operating the transmitter 21 and the receiver 22 via the drive controller 23. In addition, the main controller 41 allows for measurement based on the pulse wave Doppler method by appropriately operating the signal processor 31 to obtain a Doppler waveform or pulse waveform from the supersonic echo. The main controller 41 displays the Doppler waveform or pulse waveform on the display region of the display 42 in a visible manner to the device operator by appropriately operating the display 42. On this occasion, the main controller 41 may display, with or without rendering, the Doppler waveform, echo image, or information associated therewith on the display 42.

The main controller 41 has a memory 41a that temporarily stores, in a rendered from, the Doppler waveform (for example, vein waveform) or echo image obtained by the signal processor 31, and may display Doppler waveforms of the past or those subjected to statistical processing on the display 42 at any timing, based on an instruction from the device operator.

The main controller (waveform processor) 41 has a function of analyzing the Doppler waveform in order to automatically perform waveform tracing of the contour or the like of the Doppler waveform corresponding to one or more heartbeat or pulse periods obtained by the signal processor 31, and display the obtained trace waveform in a manner superimposed on the Doppler waveform. The trace waveform indicates the shape (specifically, steepness) of the pulse waveform, and a change in the trace waveform (specifically, decrease of steepness) indicates the change or degradation of the functional state of internal organs. The main controller 41, receiving commands via the operation panel 43 operated by the device operator, allows the device operator to use a GUI technique, or the like, to directly perform waveform tracing of the Doppler waveform being displayed on the display 42.

Figure 2:
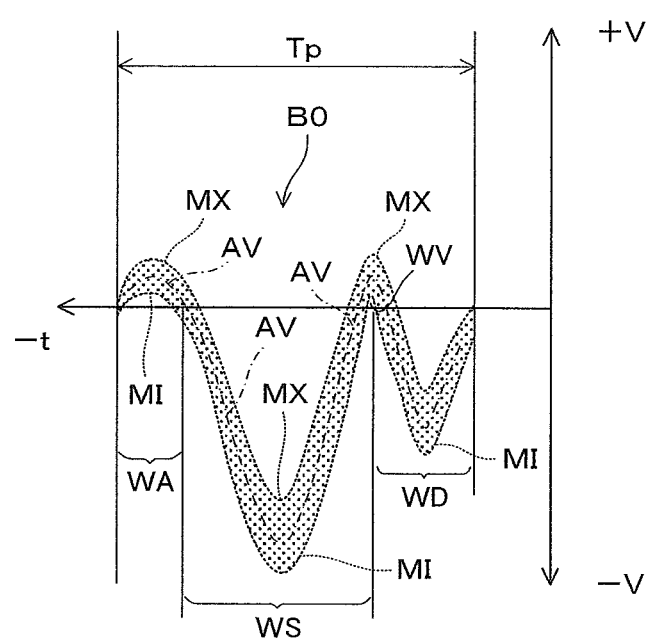
FIG. 2 is a conceptual diagram illustrating a typical example of a normal hepatic vein waveform.

FIG. 2 is a conceptual diagram illustrating a typical example of a normal hepatic vein waveform. The horizontal axis represents time t, and the vertical axis represents blood flow velocity V toward the supersonic wave probe 11. The illustrated hepatic vein waveform is of a three-phase type, and the basic vein waveform BO corresponding to one heartbeat or pulse (i.e., heartbeat period Tp) has a retrograde first waveform part WA with an ascending peak of the flow velocity, an antegrade second waveform part WS with a descending peak of the flow velocity, and an antegrade third waveform part WD with a descending peak of the flow velocity. There is a valley part WV between the second waveform part WS and the third waveform part WD, in which blood flow decreases. The first waveform part WA is a positive flow velocity region as a whole, indicating a blood flow returning toward the liver, and the second and the third waveform parts WS and WD are negative flow velocity regions as a whole, indicating a blood flow returning toward the heart. There is a tendency that the first waveform part WA is firstly lost as liver fibrosis progresses, then the boundary between the second and the third waveform parts WS and WD is lost as the liver fibrosis further progresses, and finally it becomes difficult to distinguish the second and the third waveform parts WS and WD. The hepatic vein waveform is a band- or belt-like form having a fluctuating component or a noise component of the velocity within a largely fluctuating waveform component, and there exists a large difference between the maximum value and the minimum value at each time phase.

When performing waveform tracing of a hepatic vein waveform illustrated in FIG. 2, it is necessary to take into account the fluctuation component or the noise component of the velocity. The main controller (waveform processor) 41 is, firstly, capable of performing a process such as tracing a maximum value MX at each time phase in the hepatic vein waveform. In addition, the main controller (waveform processor) 41 is, secondly, capable of performing a process of tracing a minimum value MI at each time phase in the hepatic vein waveform. Furthermore, the main controller (waveform processor) 41 is, thirdly, capable of performing a process of tracing a mean value AV between the minimum value and the maximum value at each time phase in the hepatic vein waveform. Moreover, the main controller (waveform processor) 41 is, fourthly, capable of performing a process of tracing the absolute maximum velocity (not illustrated) at each time phase in the hepatic vein waveform. The trace of the absolute maximum flow velocity, which may be regarded as one that selects the outside where swing of the waveform is larger, can be said that characteristics of the hepatic vein waveform is extracted in an outstanding manner. In the case of tracing the absolute maximum flow velocity, specifically, an envelope is extracted at the high-velocity side of the absolute value of the first waveform part WA and, when there exists the second waveform part WS, an envelope is extracted at the high-velocity side of the absolute value of the second waveform part WS and, when there exists the third waveform part WD, an envelope is extracted at the high-velocity side of the absolute value of the third waveform part WD. Although the aforementioned trace processing is realized by performing a process by the main controller 41 to extract an envelope for the maximum value and the minimum value of the vein waveform at each time phase, it may also be realized by permitting the device operator to trace manually via the operation panel 43 and storing the result thereof.

Waveform tracing may be performed in a variety of methods without being limited to the example described above. Specifically, the main controller 41 is also capable of performing an eclectic process such as tracing the maximum value MX in the first waveform part WA and tracing the minimum value MI in the second and the third waveform parts WS and WD. In such a case, an envelope is extracted at the high-velocity side of the first waveform part WA and, when there exists the second waveform part WS, an envelope is extracted at the low-velocity side of the second waveform part WS and, when there exists the third waveform part WD, an envelope is extracted at the low-velocity side of the third waveform part WD. The process can be seen as a type of process that uses the absolute maximum flow velocity described above.

The main controller (not illustrated) 41 determines the coefficient of variation, i.e., the CV value, as a deviation index value from one or more pulse waveforms (also referred to as trace waveform or trace pattern) obtained by waveform tracing. The coefficient of variation or the CV value (=standard deviation/mean velocity), indicating an unevenness of the blood flow velocity in the pulse waveform of interest is given by the following expression (1):

$$CV = \frac{\sqrt{\left|\frac{1}{n}\sum_{i=1}^{n}(V_i - V_{m\_peak})^2\right|}}{V_{m\_peak}} \qquad (1)$$

$$= \frac{\sqrt{\left|\frac{1}{n}\sum_{i=1}^{n}(V_i^2 - V_{m\_peak})^2\right|}}{V_{m\_peak}}$$

where, n is the number of samples of the blood velocity value forming the pulse waveform, $V_i$ is the blood flow velocity (m/s) in the pulse waveform, and $V_{m\_peak}$ is the mean value of the blood flow velocity (m/s). The coefficient of variation (CV value) can be expressed by the following expression (2), using the mean pressure gradient MPG (mmHg) according to the simplified Bernoulli equation.

$$CV = \frac{\sqrt{\left|\frac{1}{4}MPG - (V_{m\_peak})^2\right|}}{V_{m\_peak}} \qquad (2)$$

The mean pressure gradient MPG is a parameter indicating the pressure difference between different sites, and can be approximately calculated as a pressure gradient ΔP (mmHg) =4V², with V being the blood flow velocity at the site of interest according to the simplified Bernoulli equation. In the present embodiment, the main controller 41 is capable of calculating the pressure gradient MPG from the trace waveform, i.e., the pulse waveform after the waveform tracing, and also capable of obtaining, from the trace waveform or pulse waveform after the waveform tracing, the CV value relating to the unevenness thereof, i.e., unevenness of the blood flow velocity.

The CV value obtained as described above and the deviation index value including the value obtained by appropriately processing the CV value tends to become smaller with increasing tissue elasticity or tissue stiffness of an internal organ such as liver fibrosis, i.e., the degree of progress of a disease or change of the internal organ, and using the coefficient of variation of the pulse waveform or CV value makes it easier to evaluate the degree of progress of a disease or change at the target site or the inspected site such as the liver or the like.

Figure 3:
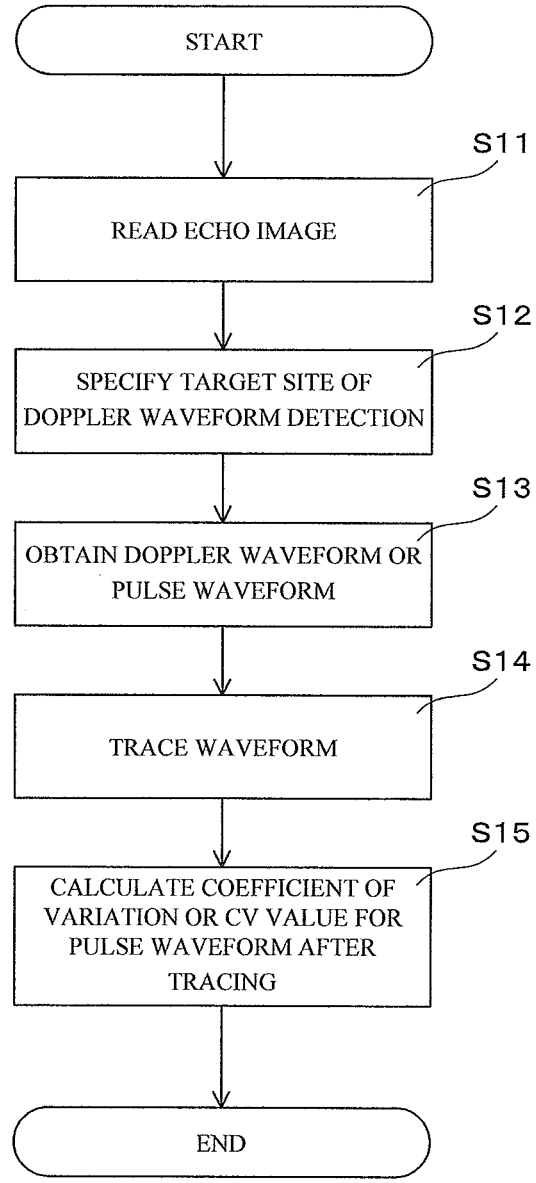
FIG. 3 is a conceptual diagram explaining an exemplary tissue elasticity measurement method using a measurement device of an embodiment.
Figure 4:
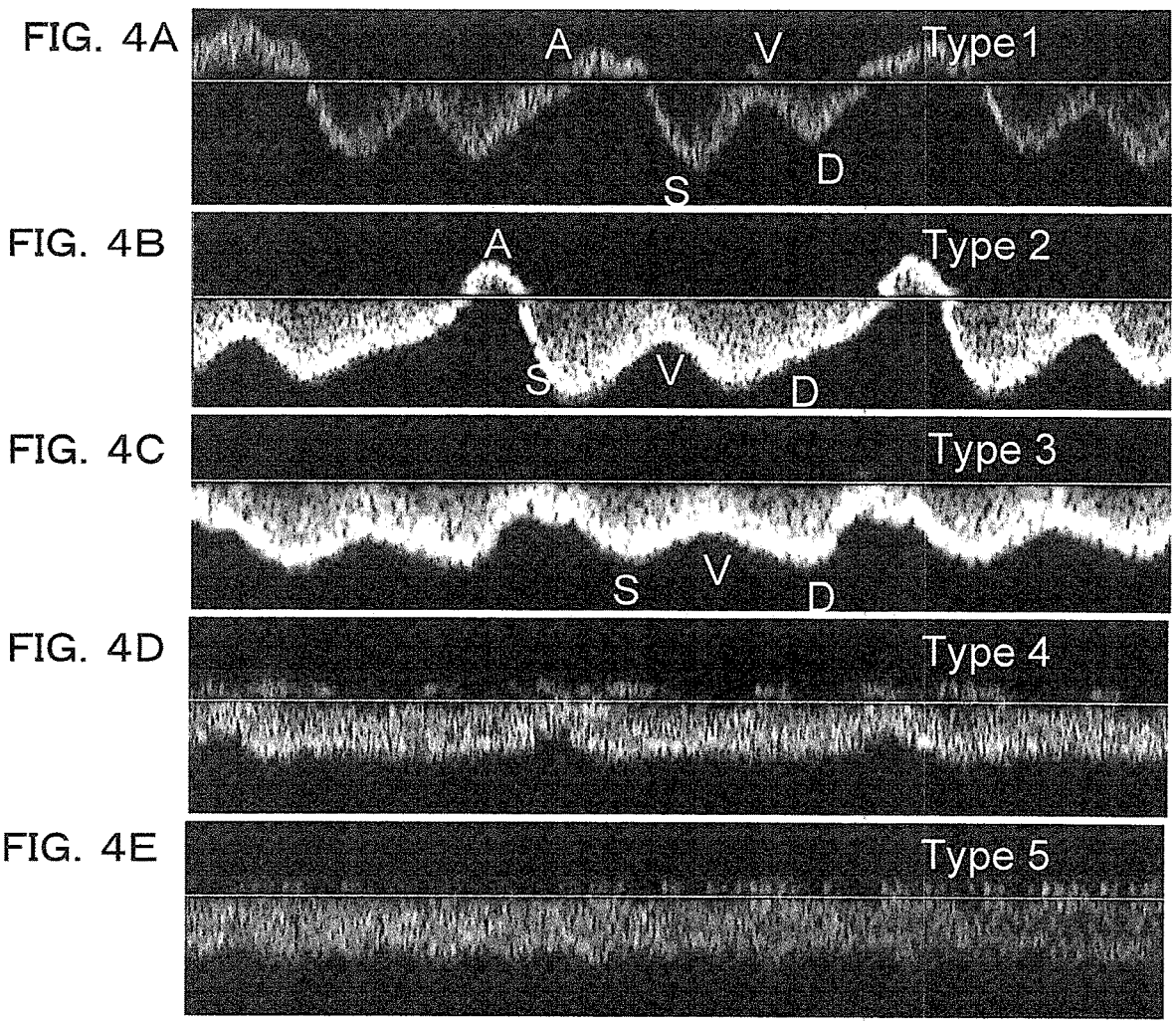
FIGS. 4A to 4E are explanatory diagrams of changes and classification (types 1 to 5) of the hepatic vein waveform associated with the progress of liver fibrosis.

In the following, the tissue elasticity measurement method using the measurement device 100 illustrated in FIG. 1 will be described, referring to FIG. 3.

First, the device operator or measurer presses the supersonic wave probe 11 against a body surface of a target site or an inspected site of a subject, and reads an echo image (Step S11). On this occasion, in a case where the inspected site is a hepatic vein, the supersonic wave probe 11 is placed so as to be appropriate relative to the direction in which the hepatic vein extends.

Next, the measurer, using the display 42 and the operation panel 43, specifies the inspected site or measurement point of the subject as the target of Doppler waveform detection (Step S12), while observing the echo image. Specification of the inspected site is achieved by an operation such as marking the echo image displayed on the display 42.

Subsequently, the main controller 41 obtains the pulse wave Doppler method-based Doppler waveform or pulse waveform for the inspected site or measurement point targeted at step S12 by appropriately operating the signal processor 31 (Step S13).

Next, the main controller (waveform processor) 41 automatically performs waveform tracing of the contour or the like of the Doppler waveform obtained at step S13, and displays the obtained pulse waveform after the tracing, i.e., the trace waveform in a manner superimposed on the original Doppler waveform (Step S14).

Furthermore, the main controller (waveform processor) 41 performs a process of calculating the coefficient of variation or CV value for the vein waveform after the tracing, i.e., the trace waveform (Step S15), and evaluates the degree of increase of tissue elasticity or internal organ stiffness from the CV value, or evaluates the degree of progress of a disease or change of the internal organ. Specifically, in a case where the CV value is obtained for the hepatic vein waveform, CV value tends to become smaller in accordance with the degree of progress of liver fibrosis, and therefore it is possible to quantitatively evaluate the increase of elasticity or stiffness of a tissue, or the degree of progress of liver fibrosis, based on the CV value. Note that, in actual measurement or a diagnosis, it is possible to use a variety of deviation indexes values subjected to a process such as taking the reciprocal of, or logarithmically converting the CV value, or the like.

In addition, setting a plurality of threshold values for the CV value obtained as described above allows for converting the state of increase or change of tissue elasticity into a level classification or a discrete category variable such as three stages, five stages, or the like.

According to the tissue elasticity measurement device 100 described above, the information processor 100b calculates, from the pulse waveform obtained by the pulse wave Doppler method, the coefficient of variation (CV value) or the deviation index value resulted from processing the coefficient of variation, and therefore allows for quantitatively evaluating changes in the shape of the pulse waveform (specifically, decrease of steepness) with a good reproducibility. The coefficient of variation corresponding to the shape of the pulse waveform (specifically, steepness) tends to become smaller with increasing tissue elasticity or tissue stiffness such as liver fibrosis, and the use of the coefficient of variation of the pulse waveform or deviation index value makes it easier to evaluate an increase in the tissue elasticity, and further the degree of progress of a disease or change of the biological tissue.

In the following, a static-tissue elasticity measurement method or diagnosis method according to the present invention will be described, referring to specific test examples.

FIGS. 4A to 4E illustrate changes in the hepatic vein waveform associated with the progress of liver fibrosis, as types-1 to 5 hepatic vein waveforms in descending order. The type-1 waveform illustrated in FIG. 4A has a retrograde partial wave A and antegrade partial waves S and D corresponding to the first to the third waveform parts WA, WS, and WD described in FIG. 2, and a valley-shaped part V between the antegrade partial waves S and D where the velocity decreases. Although the type-2 waveform illustrated in FIG. 4B has a partial waves A, S and D similarly as described above, a part V, which is a transition portion between the partial waves S and D, has descended below the zero-velocity base line. In the case of the type-3 waveform illustrated in FIG. 4C, the partial wave A has disappeared, leaving only the partial waves S and D forming a two-phase wave. In the case of the type-4 waveform illustrated in FIG. 4D, the part V between the partial waves S and D has disappeared, and there is no distinction between the partial waves S and D. In the case of the type-5 waveform illustrated in FIG. 4E, distinction between the partial waves S and D becomes difficult. As thus described, the method of classifying the changes in the hepatic vein waveform into five types is not common, and the steep type-1 illustrated in FIG. 4A has been conventionally regarded as a typical three-phase wave in a state in which liver fibrosis exhibits little progress, the relatively gentle type-3 illustrated in FIG. 4C as a typical two-phase wave in a state in which liver fibrosis has progressed to a certain degree, and the flat type-5 illustrated in FIG. 4E as a typical single-phase wave in a state in which liver fibrosis has severely progressed.

Figure 5:
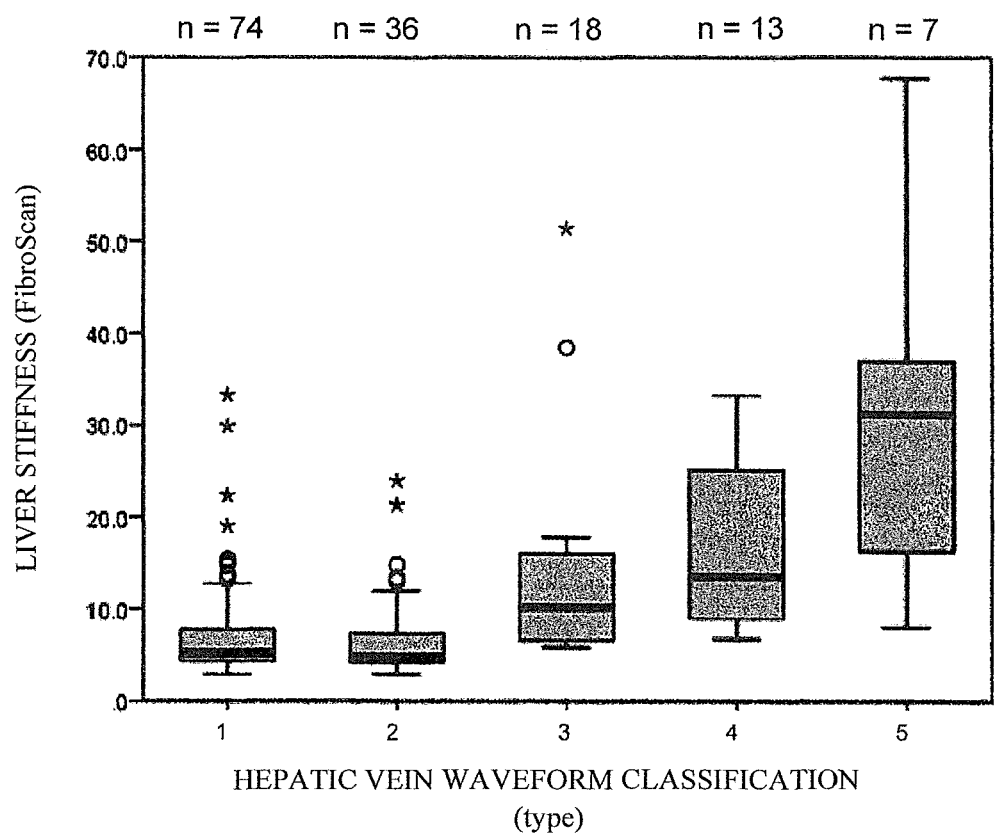
FIG. 5 is an explanatory diagram of the relation between the classification of hepatic vein waveforms and liver stiffness measured by FibroScan.

FIG. 5 is a box-and-whisker plot for explaining the relation between the classification of hepatic vein waveforms illustrated in FIGS. 4A to 4E and the liver stiffness measured by FibroScan (Fibroscan touch 502 (Echosens, Paris, France)) which is a measuring device of elastography. The values of n above the types 1 to 5 along the horizontal axis indicates the number of subjects in a normal stiffness range. In addition, the boxes in the chart indicates a quartile range (IQR), with the marks ★ and ○ in the chart indicating an outlier value beyond the maximum value and the minimum.

The relation between the hepatic vein waveform and the liver stiffness illustrated in FIG. 5 was obtained by performing abdominal echography and liver stiffness measurement for 148 chronic liver disease patients. As a specific test method, abdominal echography and hepatic vein pulse Doppler measurement were performed using Toshiba Medical Systems Corporation Aplio 300 or Aplio 500 for patients after four-hour or more fasting. In addition, liver stiffness measurement using Fibroscan touch 502 (Echosens, Paris, France) was performed on the same day. In the pulse Doppler measurement, the right hepatic vein or the middle hepatic vein was delineated from the right intercostal as a target region for measuring the hepatic vein waveform, and a measurement point was set within a distance of 5 cm from the part branching with the inferior vena cava. Measurement of the vein waveform was performed in a supine position with normal breathing. Manual tracing was performed for the stored vein waveform as much as one heartbeat, and the CV (coefficient of variation) was calculated based on the tracing. When performing tracing of a vein waveform, the absolute maximum flow velocity (outside of the waveform) was used.

Figure 6A:
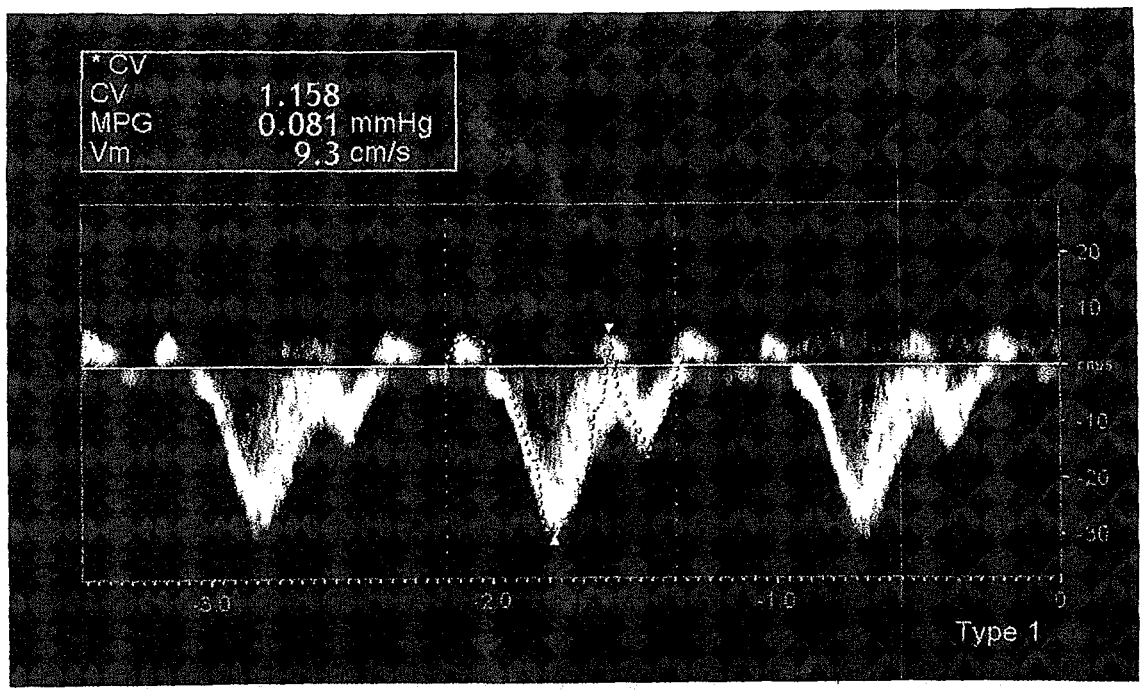
FIG. 6A illustrates an example of a type-1 hepatic vein waveform used for measurement of the CV value.
Figure 6B:
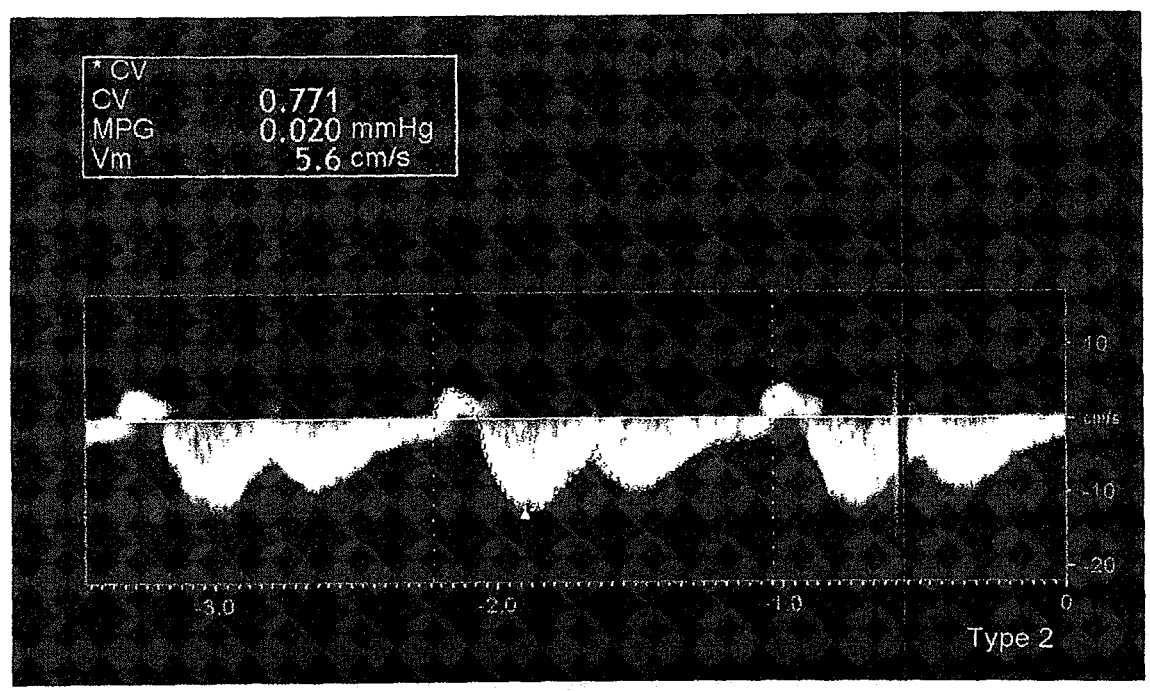
FIG. 6B illustrates an example of a type 2 hepatic vein waveform used for measurement of the CV value.
Figure 7A:
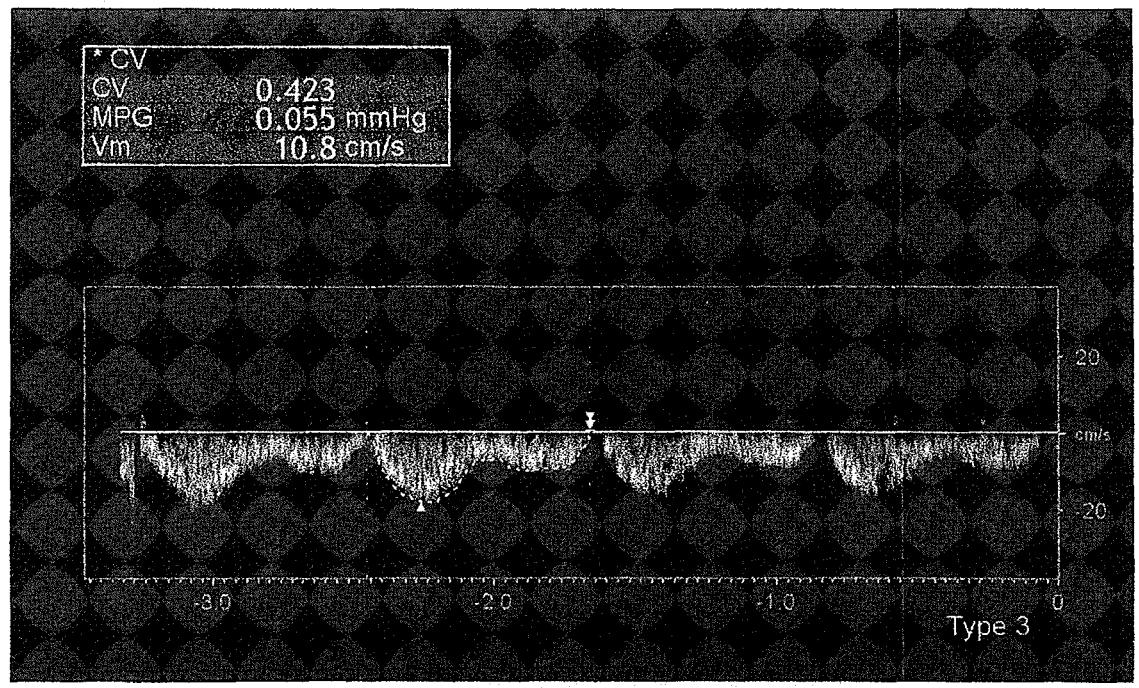
FIG. 7A illustrates an example of a type-3 hepatic vein waveform used for measurement of the CV value.
Figure 7B:
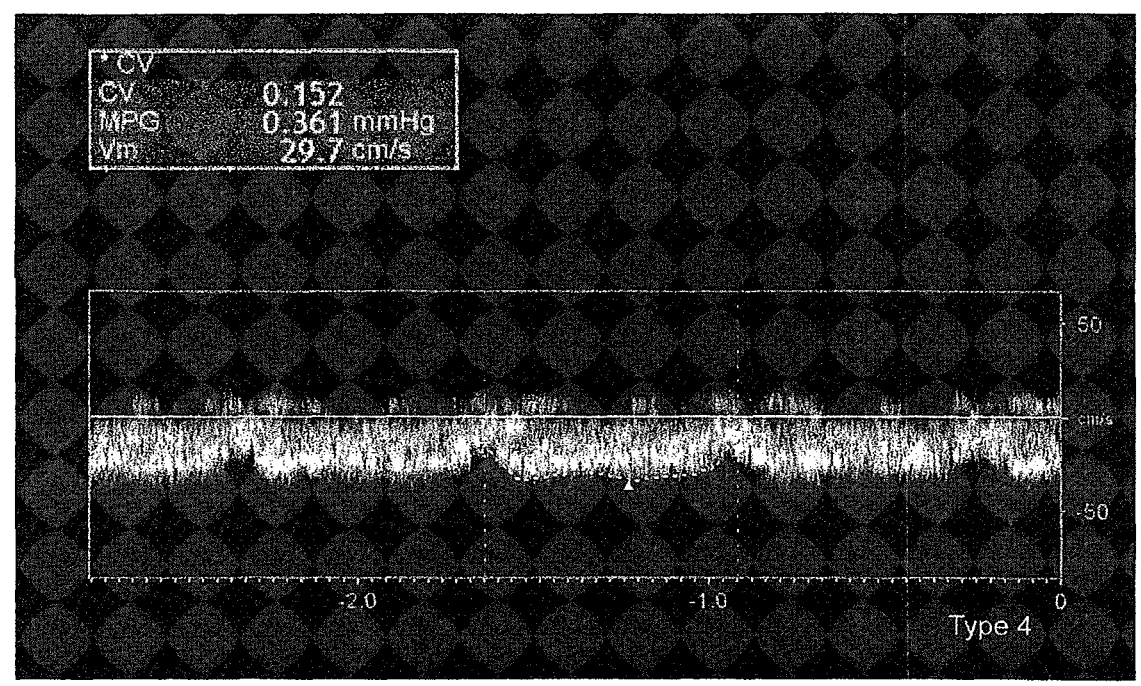
FIG. 7B illustrates an example of a type-4 hepatic vein waveform used for measurement of the CV value.
Figure 8:
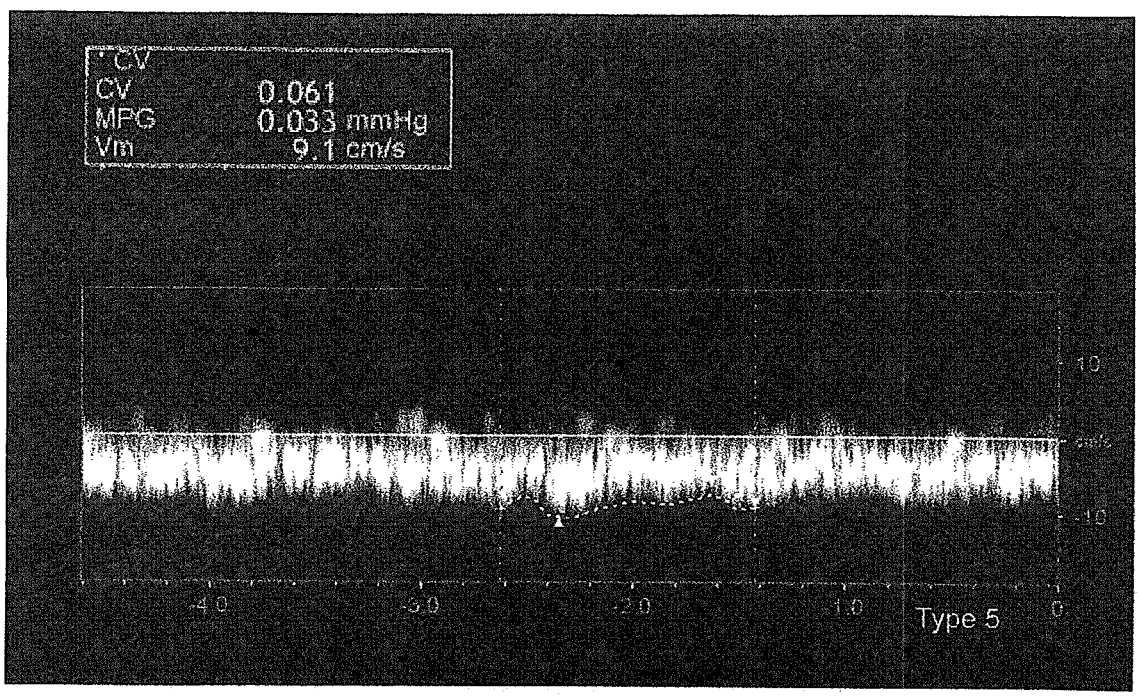
FIG. 8 illustrates an example of a type-5 hepatic vein waveform used for measurement of the CV value.

FIG. 6A illustrates an example of a type-1 hepatic vein waveform obtained by a test, in which a steep three-phase trace trajectory or trace waveform (dashed line) used for measurement of the CV value is displayed within the hepatic vein waveform. FIG. 6B illustrates an example of a type-2 hepatic vein waveform, in which a relatively gentle three-phase trace trajectory or trace waveform (dashed line) used for measurement of the CV value is displayed within the hepatic vein waveform. FIG. 7A illustrates an example of a type-3 hepatic vein waveform, in which a gentle two-phase trace trajectory or trace waveform (dashed line) used for measurement of the CV value is displayed within a hepatic vein waveform. FIG. 7B illustrates an example of a type-4 hepatic vein waveform, in which a single-phase trace trajectory or trace waveform (dashed line) with slight ups and downs remaining therein used for measurement of the CV value is displayed within the hepatic vein waveform. FIG. 8 illustrates an example of a type-5 hepatic vein waveform, in which a flat single-phase trace trajectory or trace waveform (dashed line) used for measurement of the CV value is displayed within the hepatic vein waveform.

Figure 9:
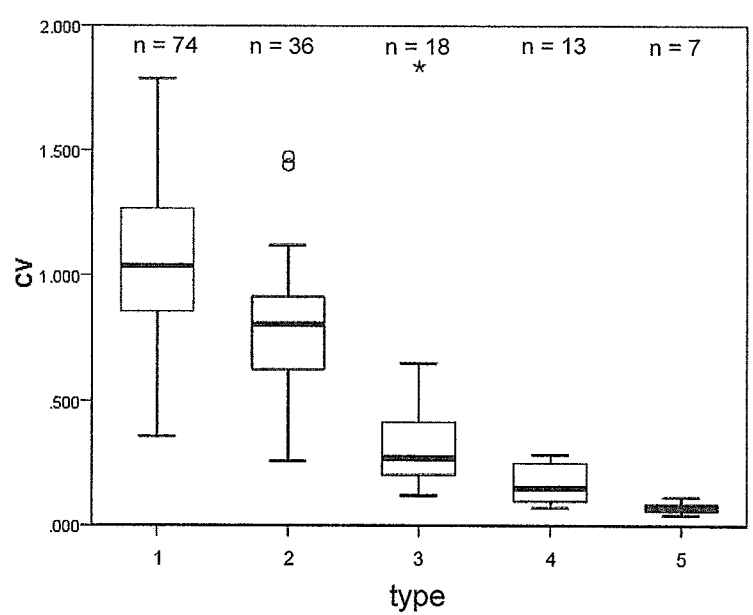
FIG. 9 is a statistical diagram displaying the CV values obtained for a number of hepatic vein waveforms of the types 1 to 5.

FIG. 9, corresponding to FIG. 5, illustrates, in a form of a chart, CV values obtained for a number of hepatic vein waveforms of the types 1 to 5. Here, the horizontal axis indicates waveform types preliminarily classified by eyesight, and the vertical axis indicates CV values obtained by tracing the hepatic vein waveform by schemes exemplified in FIGS. 6A, 6B, 7A, 7B, and 8. As can be clearly seen in FIG. 9, there is an obvious correlation between hepatic vein waveforms of the types 1 to 5 and CV values obtained by the aforementioned schemes, and there is a tendency that the initial CV value quickly decreases, and subsequently the CV value gradually and slowly decreases along with the shift from type 1 to type 5.

Figure 10A:
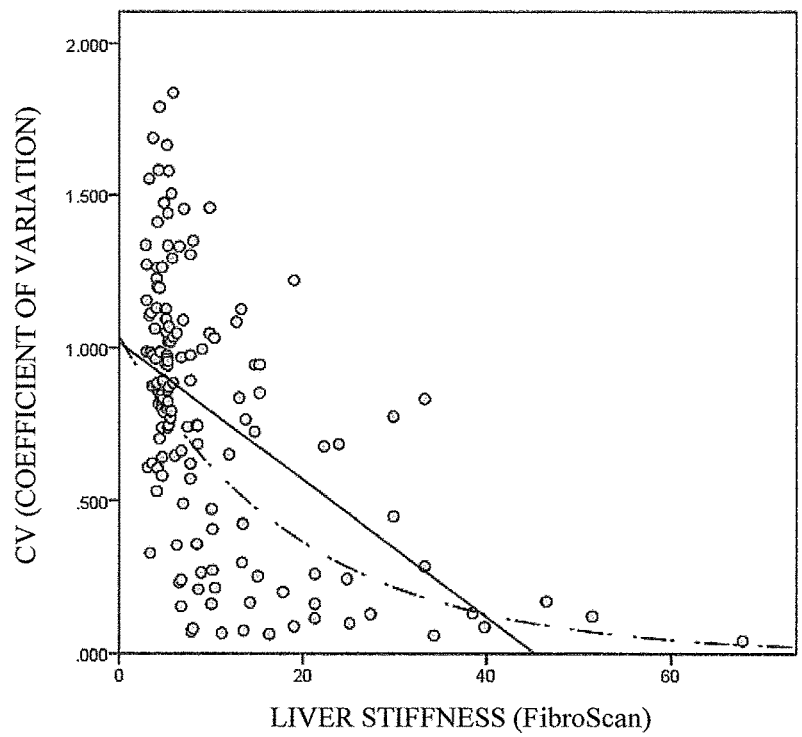
FIG. 10A is a chart indicating the relation between the liver stiffness measured by FibroScan and the CV values.
Figure 10B:
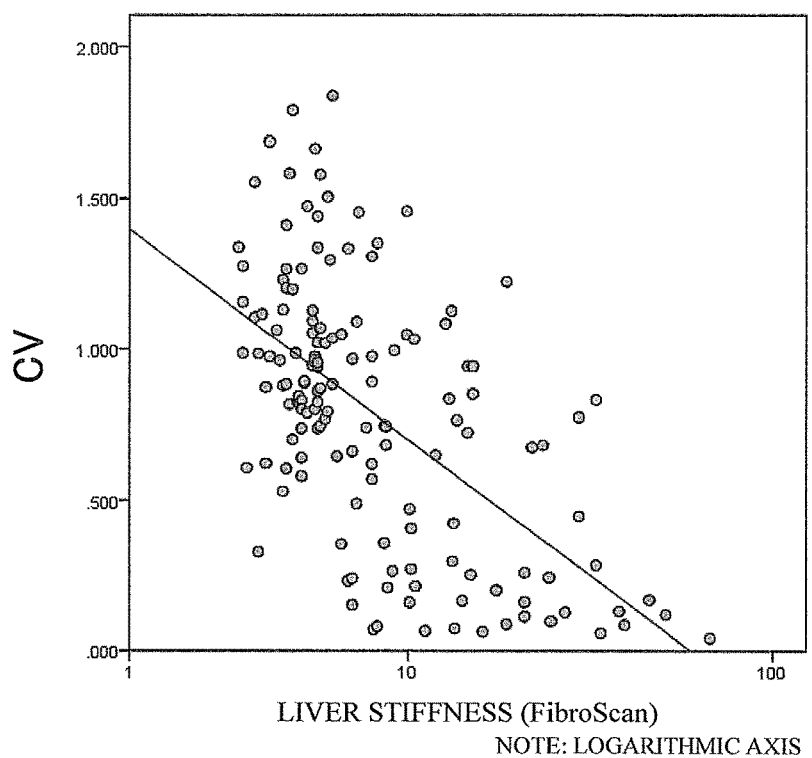
FIG. 10B is a chart indicating the relation between the logarithmic values of liver stiffness measured by FibroScan and the CV values.

FIG. 10A is a scatter plot indicating the relation between the liver stiffness measurement values using FibroScan and the CV values obtained by tracing the hepatic vein waveform, and FIG. 10B is a scatter plot or chart indicating the relation between logarithmic values of liver stiffness measurement value using FibroScan and the CV values obtained by tracing the hepatic vein waveform. As can be clearly seen by comparing them, there is observed a significant correlation between the CV values and the liver stiffness measurement values of FibroScan and, when logarithmically converted as in FIG. 10B, it is observed that an inverse proportional relation holds.

Figure 11:
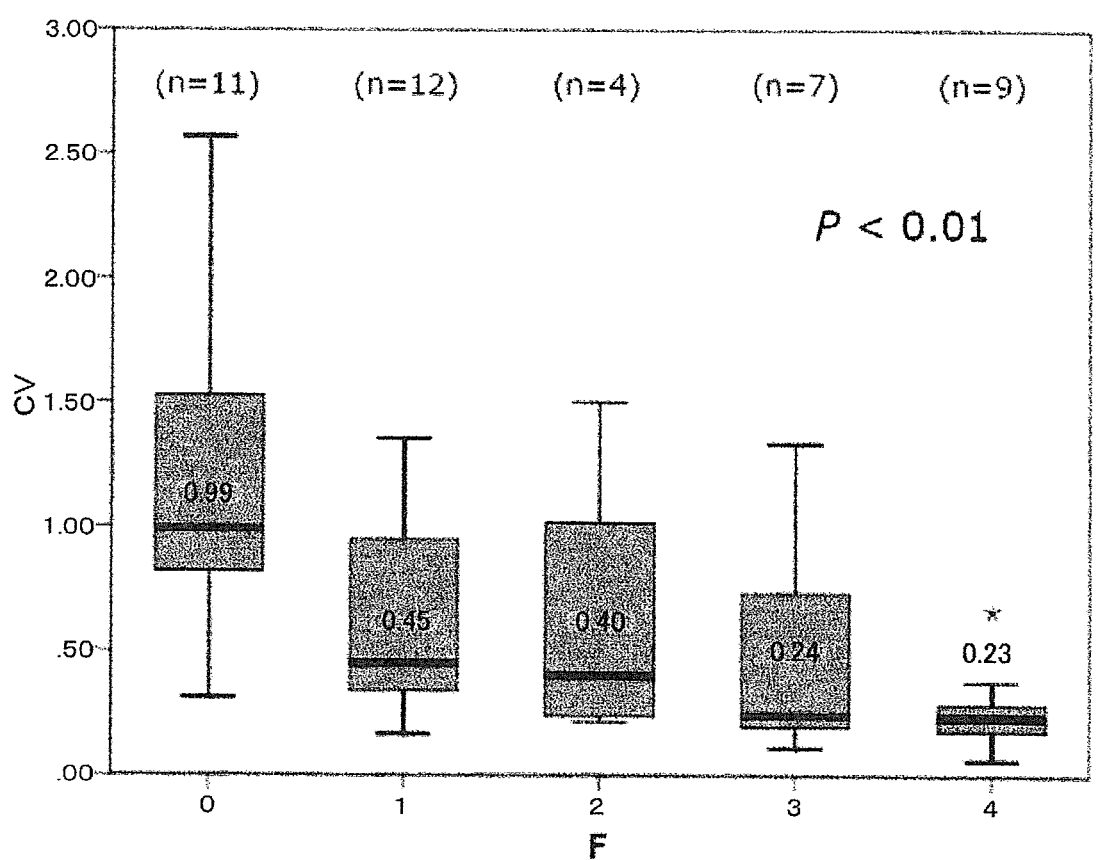
FIG. 11 is an explanatory diagram of the relation between the CV values and the result of liver biopsy.

FIG. 11 illustrates a box-and-whisker plot for explaining the relation between the CV values calculated from hepatic vein waveforms obtained by supersonic wave inspection on subjects, i.e., chronic liver disease patients subjected to liver biopsy at the University of Tokyo Hospital, and the degree of histological fibrosis obtained by performing liver biopsy. The horizontal axis indicates the degree of fibrosis of liver tissue determined by a pathologist, in which a fibrosis index value F=0 indicates the normal state without fibrosis, and indicates that the larger the numerical values of the fibrosis index values F=1 to 4, the more the fibrosis has progressed. Specifically, F=1 indicates a state in which expansion of fibrosis is observed in the portal area, F=2 indicates a state in which bridging fibrosis has been formed, F=3 indicates a state in which bridging fibrosis accompanying lobule distortion has been formed, and F=4 indicates a state of hepatic cirrhosis. In the chart, n indicates the number of subjects. In liver biopsy, a needle was pierced into the liver to collect tissue and the degree of fibrosis was observed by eyesight via a microscope for a total of 43 subjects. Liver biopsy allows for directly observing liver tissue by eyesight and therefore is the most certain inspection method. The fibrosis index values F=1 to 4 corresponds to the hepatic vein waveforms of the types 2 to 5 illustrated in FIGS. 4B to 4E. The CV values have correlation with the fibrosis index values F provided by liver biopsy, and it can be seen that the larger the fibrosis index values F, the more the CV values decrease in an inversely proportional manner.

In the following, the diagnosability using the CV values and the diagnosability using the stiffness measurement values based on FibroScan are compared, referring to the fibrosis index values F obtained in liver biopsy described in FIG. 11.

Figure 12A:
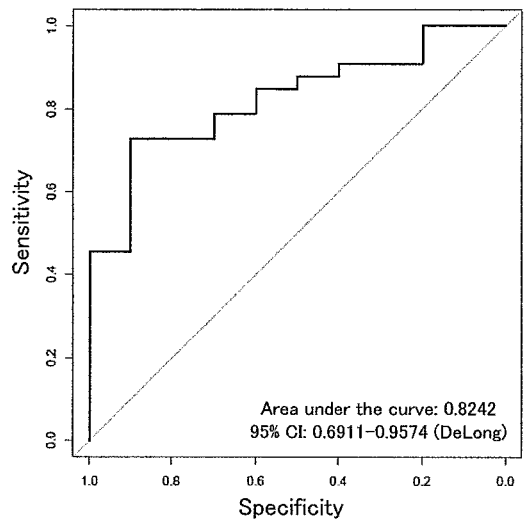
FIGS. 12A and 12B illustrate an ROC curve and analysis result thereof comparing the diagnosability according to CV values and stiffness measurement values, and a significance test performed by the DeLong method, with regard to the distinction between F=0 and F=1 to 4.
Figure 12B:
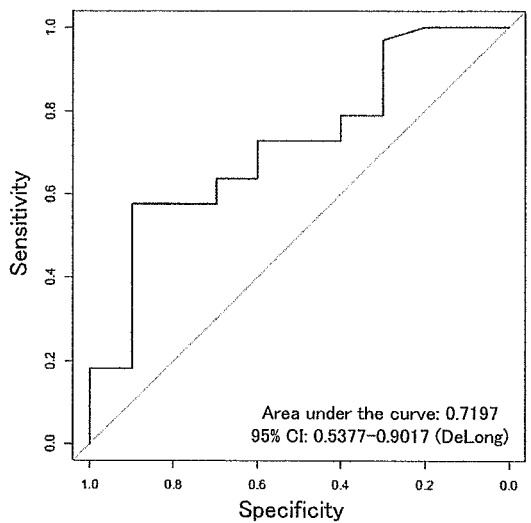

FIG. 12A is an ROC curve (Receiver Operating Characteristic Curve) indicating the diagnosability relating to the distinction between F=0 and F=1 to 4 in the case of using the CV values, and FIG. 12B is an ROC curve indicating the diagnosability relating to the distinction between F=0 and F=1 to 4 in the case of using the stiffness measurement value based on FibroScan. Here, the horizontal axis indicates specificity, and the vertical axis indicates sensitivity. It can be seen from the comparison that the value of AUC (area under the curve) is significantly larger in the case of using the CV values. Comparison of the precisions using the DeLong test for the two AUCs resulted in a p-value of 0.01 or less, exhibiting a significantly higher diagnosability by the CV.

Figure 12C:
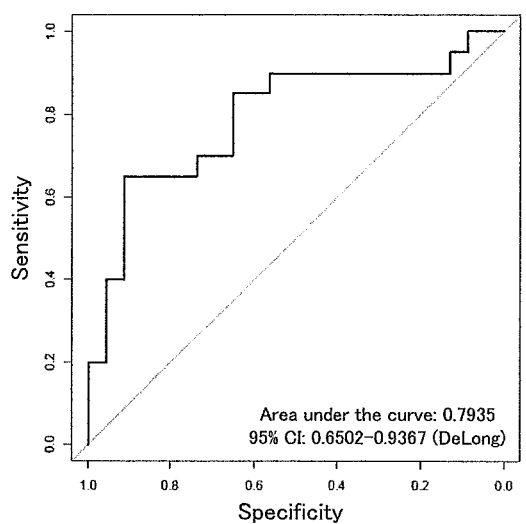
FIGS. 12C and 12D illustrate an ROC curve and analysis result thereof comparing the diagnosability according to CV values and stiffness measurement values, and a significance test performed by the DeLong method, with regard to the distinction between F=0 to 1 and F=2 to 4.
Figure 12D:
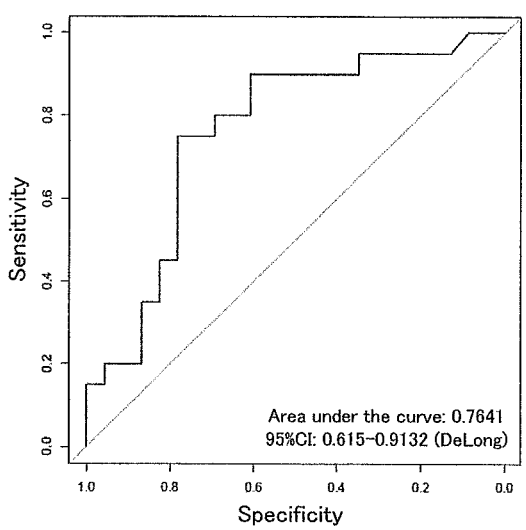

FIG. 12C is an ROC curve indicating the diagnosability relating to the distinction between F=0 to 1 and F=2 to 4 in the case of using the CV values, and FIG. 12D is an ROC curve indicating the diagnosability relating to the distinction between F=0 to 1 and F=2 to 4 in the case of using the stiffness measurement value based on FibroScan. It can be seen from the comparison that the value of AUC is larger in the case of using the CV values. Comparison of the precisions for the two AUCs resulted in a p-value of 0.01 or less.

Figure 13A:
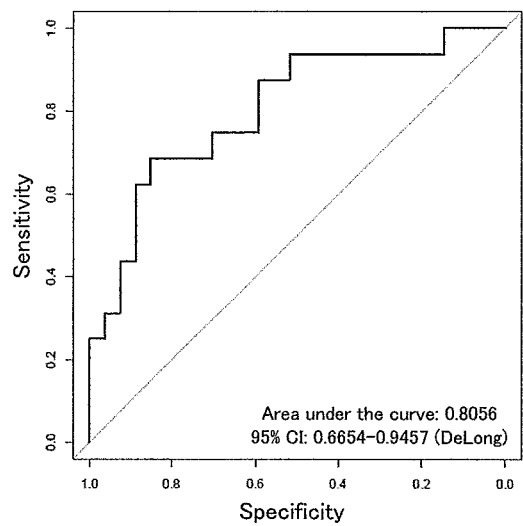
FIGS. 13A and 13B illustrate an ROC curve and analysis result thereof comparing the diagnosability according to CV values and stiffness measurement values, and a significance test performed by the DeLong method, with regard to the distinction between F=0 to 2 and F=3 to 4.
Figure 13B:
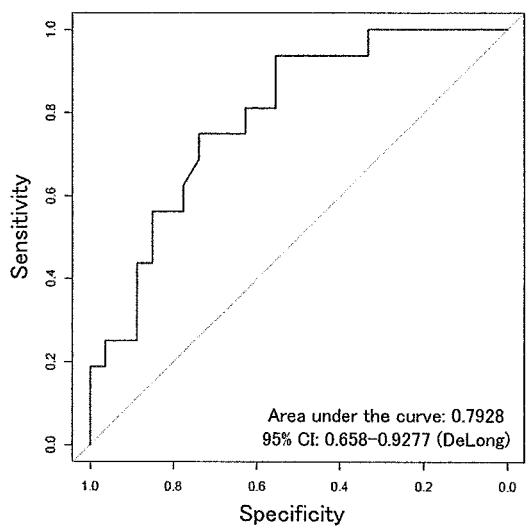

FIG. 13A is an ROC curve indicating the diagnosability relating to the distinction between F=0 to 2 and F=3 to 4 in the case of using the CV values, and FIG. 13B is an ROC curve indicating the diagnosability relating to the distinction between F=0 to 2 and F=3 to 4 in the case of using the stiffness measurement value based on FibroScan. It can be seen from the comparison that the value of AUC is larger in the case of using the CV values. Comparison of the precisions for the two AUCs resulted in a p-value of 0.01 or less.

Figure 13C:
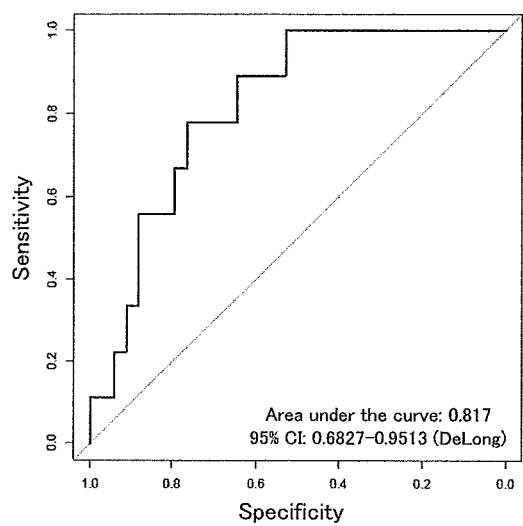
FIGS. 13C and 13D illustrate an ROC curve and analysis result thereof comparing the diagnosability according to CV values and stiffness measurement values, and a significance test performed by the DeLong method, with regard to the distinction between F=0 to 3 and F=4.
Figure 13D:
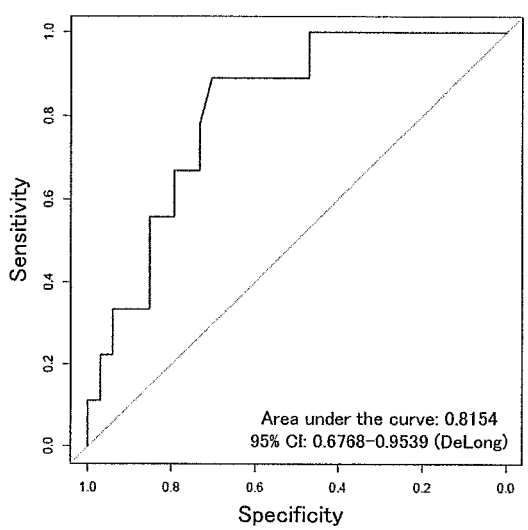

FIG. 13C is an ROC curve indicating the diagnosability relating to the distinction between F=0 to 3 and F=4 in the case of using the CV values, and FIG. 13D is an ROC curve indicating the diagnosability relating to the distinction between F=0 to 3 and F=4 in the case of using the stiffness measurement value based on FibroScan. It can be seen from the comparison that the value of AUC is slightly larger in the case of using the CV values. Comparison of the precisions for the two AUCs resulted in a p-value of 0.01 or less.

In summary, it can be seen that the diagnosability in the case of using the CV values is higher than the diagnosability in the case of using the stiffness measurement values based on FibroScan.

Although the present invention has been described above in reference to the embodiments, the present invention is not limited to the aforementioned embodiments. For example, without being limited to hepatic vein waveforms, the tissue elasticity measurement device and a measurement method of the present application may be used for measuring pulse waveforms in the carotid artery, thyroid, or the like to diagnose, from CV values thereof, the state of stiffening of the carotid artery, tumor formed in the thyroid, or the like. For example, it is common to obtain the PI (heartbeat index) and RI (resistance index) of tumor blood flow to determine the malignancy of thyroid mass, which also intends to evaluate the shape or steepness of waveforms. Also in another example, evaluation of a pulse waveform (finger plethysmogram) that appears in an artery of a finger tip is commonly used to determine arteriosclerosis. Such a biological signal such as a pulse wave or neural transmission in such an organism contributes to diagnosis via determination of the shape, steepness, or gentleness of its waveform, making it possible to perform quantitative evaluation based on changes in the waveform using CV values, according to the present application.

Although the CV values are determined after having performed waveform tracing of the pulse waveform in the above description, the CV values may be directly determined from the pulse waveform.

The invention claimed is:
1. A tissue elasticity measurement device comprising:
a supersonic wave measuring instrument that measures a pulse waveform corresponding to a blood flow velocity using a pulse wave Doppler method, wherein the pulse waveform obtained by the supersonic wave measuring instrument using the pulse wave Doppler method is the flow velocity as a function of time; and
an information processor that calculates a coefficient of variation from a pulse waveform obtained by the supersonic wave measuring instrument,
wherein the information processor has a waveform processor that determines at least one of: an absolute maximum flow velocity, a maximum value, a minimum value, and a mean value at each time phase of a pulse waveform, and calculates a coefficient of variation from at least one of the absolute maximum flow velocity, the maximum value, the minimum value, and the mean value,
wherein the waveform processor extracts an envelope so as to conform to a standard three-phase pulse waveform having a retrograde first waveform part with an ascending peak of a flow velocity, an antegrade second waveform part with a descending peak of a flow velocity, and an antegrade third waveform part with a descending peak of a flow velocity during a heartbeat period, and calculates a coefficient of variation therefrom.

2. The tissue elasticity measurement device according to claim 1, wherein an envelope is extracted at a high-velocity side of the absolute value of the first waveform part in the case where there exists the first waveform part, an envelope is extracted at a high-velocity side of the absolute value of the second waveform part in the case where there exists the second waveform part, and an envelope is extracted at a high-velocity side of the absolute value of the third waveform part in the case where there exists the third waveform part.

3. A tissue elasticity measurement device, comprising:
a supersonic wave measuring instrument that measures a pulse waveform corresponding to a blood flow velocity by a pulse wave Doppler method; and
an information processor that calculates a coefficient of variation from a pulse waveform obtained by the supersonic wave measuring instrument,
wherein a CV value standing for the coefficient of variation, is given by the following expression:

$$CV = \frac{\sqrt{\left|\frac{1}{n}\sum_{i=1}^{n}(V_i - V_{m\_peak})^2\right|}}{V_{m\_peak}}$$

where, n is the number of samples of a pulse waveform, $V_i$ is a blood flow velocity, and
$V_{m\_peak}$ is a mean value of the blood flow velocity.

4. The tissue elasticity measurement device according to claim 3, wherein the information processor measures the coefficient of variation from a vein waveform corresponding to a plurality of heartbeat periods.

5. The tissue elasticity measurement device according to claim 3, wherein the supersonic wave measuring instrument uses fast Fourier transform to generate, from a Doppler component, a measurement value of a flow velocity for each time resolution.

6. The tissue elasticity measurement device according to claim 3, wherein the supersonic wave measuring instrument measures a vein waveform of liver.

* * * * *